Figure 1:
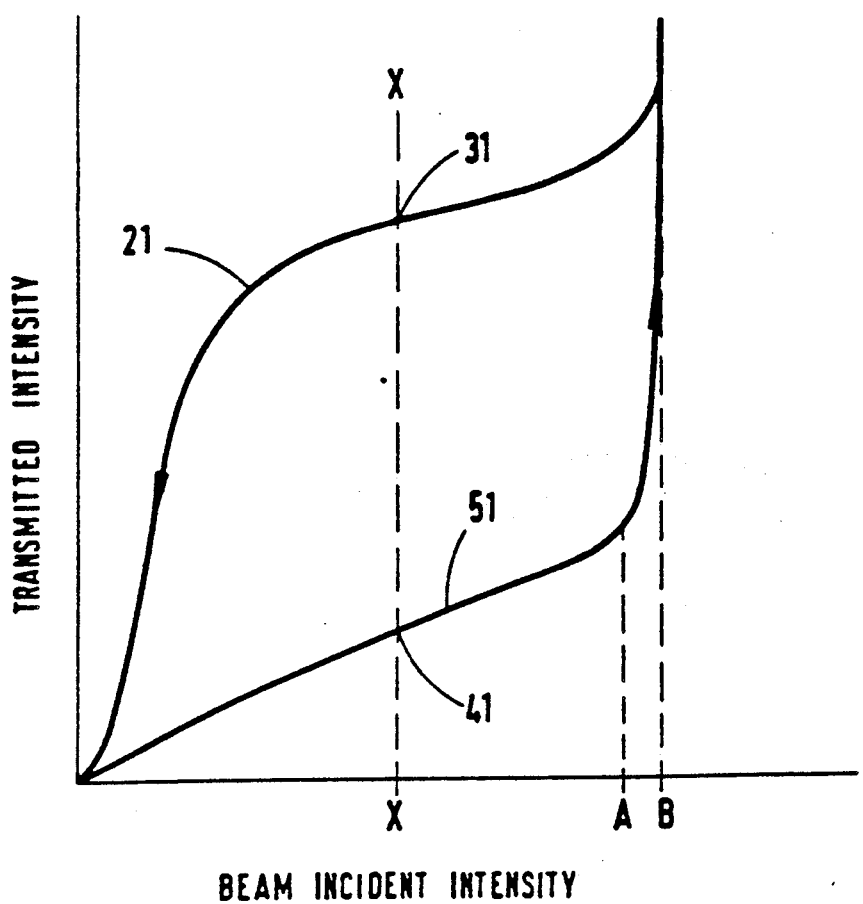

United States Patent [19]

Bennion et al.

[11] Patent Number: 4,990,287

[45] Date of Patent: Feb. 5, 1991

[54] OPTICAL DEVICES UTILIZING PHOTOCHROMIC COMPOUNDS

[75] Inventors: Ian Bennion, Ravensthorpe; Rosemary Cush, Duston; Christopher J. Groves-Kirby, Bugbrooke; Clive Trundle, Silverstone, all of England

[73] Assignee: The Plessey Company PLC, Ilford, England

[21] Appl. No.: 162,385

[22] PCT Filed: Jun. 19, 1987

[86] PCT No.: PCT/GB87/00428

§ 371 Date: Feb. 19, 1988

§ 102(e) Date: Feb. 19, 1988

[87] PCT Pub. No.: WO87/07963

PCT Pub. Date: Dec. 30, 1987

[30] Foreign Application Priority Data

Jun. 19, 1986 [GB] United Kingdom ............... 8614972

[51] Int. Cl.$^5$ .............................................. G02B 5/23
[52] U.S. Cl. .................................... 252/586; 350/266; 350/353; 350/354; 549/71; 549/70
[58] Field of Search .................. 252/582, 589, 586; 350/266, 267, 353, 354; 549/70, 71

[56] References Cited

U.S. PATENT DOCUMENTS 3,565,814  2/1971  Pellon .................................. 252/586
4,818,096  4/1989  Heller et al. ......................... 351/163

OTHER PUBLICATIONS

Brown, G. H. in Photochromism, Brown, G. H. ed., Wiley, New York, 1971, Chapter. 1.
Kirkby, C. J. H.; Cush, R.; Bennion, I. Optics. Comm. 56, (4) 288, 1985.
Mitsuhashi, Y. Optics Lett. 6(3) 111, 1981.
LeNoble, C.; Becker, R. S.; J. Photochem. 33 (1986) 187–197.

Primary Examiner—John S. Maples
Assistant Examiner—Richard Treanor
Attorney, Agent, or Firm—Sughrue, Mion, Zinn, Macpeak & Seas

[57] ABSTRACT

An optical resonant assembly which comprises a plurality of partially light-transmitting mirrors, a layer of photochromic material disposed between the mirrors, a light source providing a light beam of variable intensity incident on the layer of photochromic material and detecting means for determining transmittance values of said incident beam at different intensity levels, said photochromic material having a low quantum yield for bleaching with light of a wavelength corresponding to said light beam and being selected from pyran compounds of the general formula (I) below:

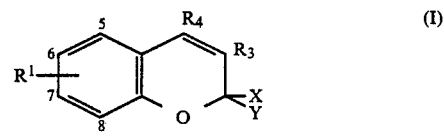

(I)

wherein X and Y together represent a spiro-adamantylidene group or a spiro-carbocyclic or heterocyclic group or X and Y independently represent hydrogen, alkyl (preferably lower alkyl having 1 to 5 carbon atoms) or phenyl and $R_3$ and $R_4$ each independently represent hydrogen, alkyl, aralkyl, aryl, halogen or a heterocyclic group and $R^1$ reprsents hydrogen, lower alkyl, aryl, aloxy, alkyl- or dialkyl amino, halogen, or heterocyclic or $R^1$ represents a fused benzene ring at the 5, 6 or 7, 8 positions.

14 Claims, 1 Drawing Sheet

OPTICAL DEVICES UTILIZING PHOTOCHROMIC COMPOUNDS

This invention relates to optical devices, particularly optical resonant assemblies, which utilise photochromic compounds.

In our U.K. patent application No. 8519711 (Publication No. 2180360), we describe an optical resonant assembly in which a photochromic compound, which is reversibly convertible between coloured and bleached states, is used to provide a plurality of stable optical transmission states.

The device described in our above patent application employs a pair of light beams, i.e. a colouring beam and a bleaching beam whose relative intensities are varied to change the light transmittance of the device.

We have now found that it is possible to construct an optical resonant device which can be switched between bistable states using only one light beam of one or more wavelengths.

This is achieved by selection of a class of photochromic compounds which have a low quantum yield for bleaching with light in the visible region.

According to the present invention there is provided an optical resonant assembly which comprises a plurality of partially light-transmitting mirrors, a layer of photochromic material disposed between the mirrors, a light source providing a light beam of variable intensity incident on the layer of photochromic material and detecting means for determining transmittance values of said incident beam at different intensity levels, said photochromic material having a low quantum yield for bleaching with light of a wavelength corresponding to said light beam and being selected from pyran compounds of the general formula (I) below:

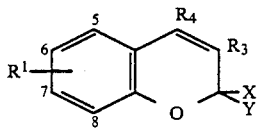

wherein X and Y together represent a spiro-adamantylidene group or a spiro-carbocyclic or heterocyclic group or X and Y independently represent hydrogen, alkyl (preferably lower alkyl having 1 to 5 carbon atoms) or phenyl and $R_3$ and $R_4$ each independently represent hydrogen, alkyl, aralkyl, aryl, halogen or a heterocyclic group and $R^1$ represents hydrogen, lower alkyl, aryl, alkoxy, alkyl- or dialkyl amino, halogen, or heterocyclic or $R^1$ represents a fused benzene ring at the 5, 6 or 7, 8 positions.

Specific examples of compounds having the desired properties are described in our U.K. patent application No. 2180360A, which discloses a series of photochromic spiro-pyrans which are represented in general terms by the following general formulae (II), (III) & (IV). in which formula (II) represents the 2H-benzopyran series and formulae (III) and (IV) represent the isomeric naphthopyran series.

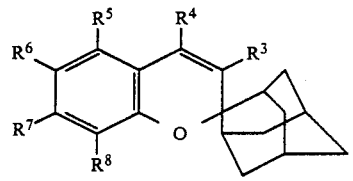

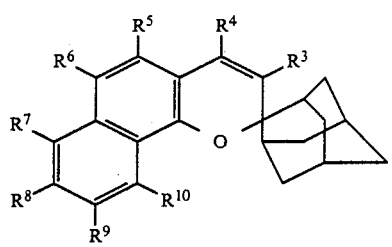

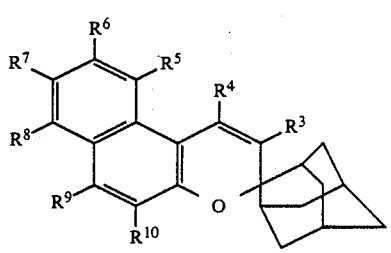

A wide variety of substituents are possible in the benzopyran or napthopyran rings. For example, the rings can be substituted in the positions represented by $R_3$ to $R_8$ (or $R_3$ to $R_{10}$) with alkyl, aryl (including substituted phenyl, e.g. alkoxyphenyl and halophenyl), alkoxy, hydroxy, alkyl or dialkylamino (e.g. dimethylamino), alkylamino-phenyl, halogen or heterocyclic groups (e.g. furyl or thienyl), with the proviso that hydroxy or alkoxy or alkyl- or dialkylamino may not be a substituent in the $R^3$ or $R^4$ position. Preferred substituents are lower alkyl (e.g. methyl or ethyl), chlorine, bromine, hydroxy, phenyl, methoxy, or methoxy phenyl groups. It is also possible to produce related series of compounds in which the basic benzopyran or naphthopyran nuclei are annelated with aryl or heterocyclic rings, such as a thiophene or furan ring.

In addition to its beneficial effect in reducing fatigue reactions, the introduction of the spiro-2-adamantane group tends to cause an increase in the quantum yield for colouring in the U.V. region, whilst providing a fast thermal fade at ambient temperature.

The following procedure can be followed to prepare adamantylidene spiro pyrans of the above general formulae. It will be appreciated that chromene is an alternative name for benzopyran. Thus, 2H-chromene is an alternative name for 2H-1-benzopyran.

CONDENSATION

Adamantanone (1 mole), the o-hydroxyacetophenone (1.1 mole) and a cyclic secondary amine (1.2 mole) are dissolved in toluene (1 cm³ for each g of reactant) and boiled (5-24 hours) until water is no longer prOduced. The water is removed as an azeotrope with toluene using a Dean and Start apparatus. Toluene is then removed under reduced pressure and the residual enamine is recrystallised from acetone or ethanol).

HYDROLYSIS

The enamine is dissolved in the minimum quantity of boiling methanol and c. hydrochloric acid (1 cm³ for every 10 g of enamine) is added. On standing, the chromanone sometimes crystallises out. If the yield of chromanone is low, the solution is heated to boiling and hot water is added until the solution becomes turbid. On cooling, the chromanone separates.

REDUCTION

Sodium borohydride (1 g per 2.5 g of chromanone) is added in small portions to the chromanone in methanol (3 cm³ per g of chromanone). When the addition is complete, the reaction mixture is boiled (2 hours) and methanol removed under reduced pressure. The residue is added to water, extracted with chloroform, dried (MgSO₄) and solvent removed, leaving the crude chromanol).

DEHYDRATION

Solvated copper sulphate, CuSO₄.5H₂O is heated strongly in a boiling tube with a bunsen burner until no more water is evolved. The resulting anhydrous copper sulphate is admixed with the chromanol (1 g per 2 g of chromanol) in a flask and heated with a bunsen burner until the organic compound melts. On cooling, the reaction mixture is extracted with chloroform, solvent is removed and the residual chromene is recrystallised from acetone or ethanol). A decolourisation with activated charcoal may be necessary.

We may also employ in the present invention structurally similar benzopyran and naphthopyran compounds to those encompassed by general formula (II), (III), and (IV) in which the adamantylidene group is replaced with a spiro-carbocyclic or spiro-heterocyclic groups or by the groups $R_1$ and $R_2$, in which $R_1$ and $R_2$ represent hydrogen, alkyl or aryl groups. For example, the benzopyran compounds corresponding to structure (II) above are as follows:

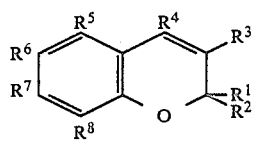

(IIa)

In structure (IIa), $R_1$ and $R_2$ may be independently selected from hydrogen, alkyl, phenyl and substituted phenyl (substituted with alkyl, alkoxy, nitro, and primary, secondary or tertiary amino or a nitrogen-containing heterocyclic substituent). Certain compounds of formula (IIa) and methods for their preparation are described in our U.K. patent application No. 8614680 entitled 'Photoreactive Lenses'. Similar compounds may be prepared to compounds of structure (II) and (III) above, in which the adamantylidene group is replaced with the groups $R_1$ and $R_2$, in which $R_1$ and $R_2$ have the significance indicated above. Examples of specific compounds or groups having the following structures (A), (B), (C) and (D).

In the structural formulae (IIa) above at least one of $R_1$ and $R_2$ preferably represent an aryl group (e.g. phenyl) having a nitrogen containing substituent in the ortho and/or para position. Examples of suitable nitrogen-containing substituents are alkyl or dialkyl amino, and morpholino, piperidino, pyridino, pyrazolino or pyrrolidino groups.

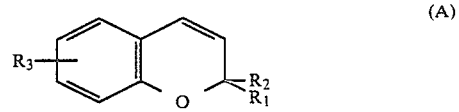

(A)

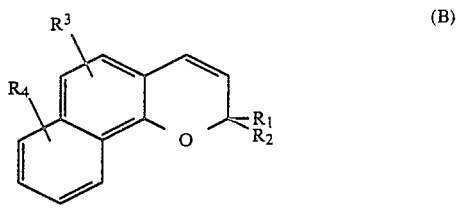

(B)

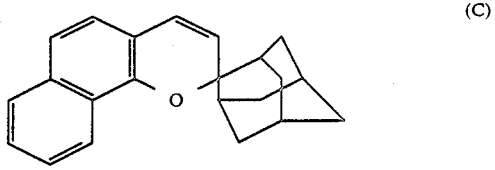

(C)

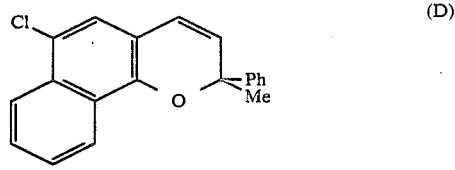

(D)

Although the compounds described above do not all possess the heliochromic properties described in our U.K. patent applications Nos: 8711511 and 8614680 (and may not possess equally pronounced photochromic properties). photochromic compounds suitable for use in the present invention may nevertheless be selected from the whole range of compounds indicated above. Many of the compOunds covered by the above structural formulae are novel compounds per se.

Compounds of the structural formulae (II), (III), & (IV) above may be prepared by an analogous method to that described above.

Alternatively, they may be prepared by a modification of the Claisen rearrangement. This process provides a general procedure for preparation of chromene derivatives and is not limited to the preparation of spiropyrans.

This Claisen rearrangement process provides a general procedure for the preparation of chromene derivatives, comprising heating a phenol with an appropriate propargyl derivative in a solvent in the presence of a suitable catalyst under mild reaction conditions.

In contrast with reaction conditions normally employed in Claisen rearrangements, the process is carried out at relatively low temperatures, e.g. in boiling xylene or toluene and in the presence of a suitable catalyst. Generally, the reaction temperature should not exceed about 180° C. and is preferably not more than 160° C. or less. The reaction can be expressed in general terms as follows:

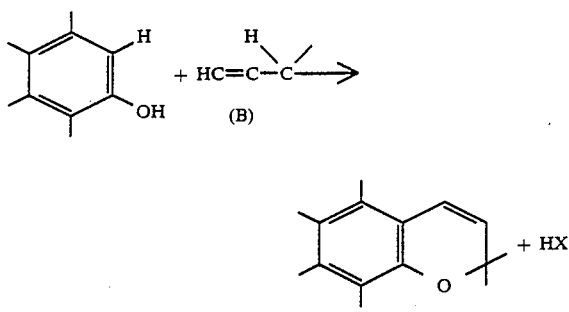

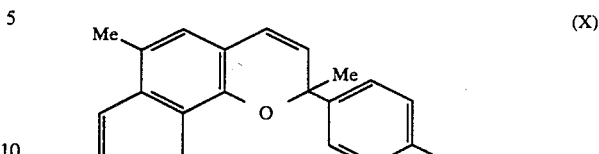

in which (A) can be any phenol and (B) a propargyl alcohol derivative, such as a propargyl acetate. The reaction is catalysed by alumina and proceeds at relatively low temperatures with a marked absence of side reactions. In place of the acetate it is possible to use any aliphatic or aromatic carboxylate, e.g. the propionate or benzoate.

Improved yields are obtained using a propargyl acetate and heating this with a phenol in a solvent such as xylene in the presence of acidic alumina as catalyst. Surprisingly, these relatively mild conditions bring about a Claisen rearrangement whereas the traditional reaction conditions, e.g. heating to about 210° C. in strongly acid conditions, caused thermal decomposition of the reactants and/or desired product.

This process provides a convenient one-step synthesis of chromenes using any phenol and the appropriate propargyl acetate or other propargyl alcohol derivative.

Propargyl acetates can be prepared by reacting an appropriate ketone with lithium acetylide. A lithium acetylide/ethylene diamine complex is added with stirring to a solution of the ketone in a suitable solvent, such as tetrahydrofuran or dimethyl sulphoxide. The product is the corresponding propargyl alcohol and the alcohol is conveniently converted to the acetate by reaction with acetyl chloride in a suitable solvent.

In the practice of this invention, the photochromic compound is supported in or on a matrix within a resonant cavity so that it can be illuminated with a beam of light of appropriate wavelength. The compound is initially converted to its coloured form, either within the cavity or prior to installation therein. For most of the photochromic compounds indicated above conversion to the coloured form is effected by irradiation with light in the blue or ultra-violet region.

A resonant cavity may be prepared by imbibing a transparent matrix with a selected photochromic material from a saturated solution of the material in an inert solvent such as fluorinated hydrocarbon, e.g. the FC series marketed by the 3M Company of the PP series marketed by ISC Chemicals. Alternatively, the material may be mixed with polymer particles and hot pressed to give a thick (2-3 mm) sample.

In a specific example, a sheet of cured polycarbonate plastics (available from P.P.G. Ltd. under the trade name CR39) was imbided with the photochromic pyran having the following formula (X) from a saturated solution of the compound in PP9 at 160° C. for 30 mins. In a second example a mixture of powdered polystyrene and the pyran (X) were hot pressed to give a clear parallel sided 2 mm thick photochromic substrate.

Figure 2:
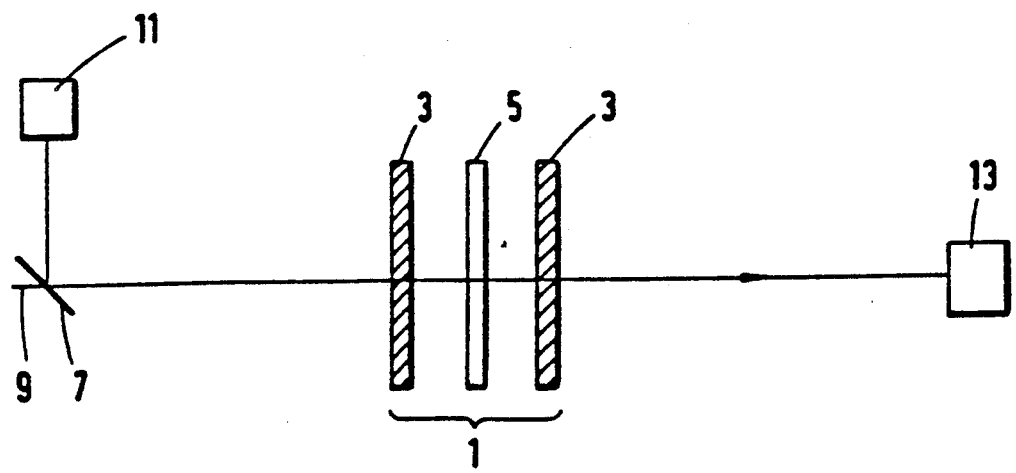

These plastic substrates were then formed into Fabry-Perot resonant cavities using a pair of partially-transmitting mirrors as illustrated in FIG. 2.

Tuning of the device through one or more resonances is then carried out by illuminating the cavity with a beam of light of a 'bleaching' wavelength; typically light in the green spectral region. A green laser of wavelength about 514 nm is suitable. If the intensity of the bleaching beam is increased, the refractive index of the compound changes and causes the cavity to be tuned through one or more resonances. As each resonance is reached, transmission of light through the device switches to a higher level. On reduction of the bleaching beam intensity the cavity is detuned through the several resonances and switching down to lower transmissions levels occurs.

FIG. 1 is a graph illustrating the behaviour of a resonant cavity in accordance with the invention when illuminated with a bleaching beam of gradually increasing intensity followed by gradual reduction of the intensity of the bleaching beam. Curve 51 shows the effect on the transmission of light through the device of a gradual increase in the incident intensity of the bleaching radiation. As the incident intensity increases past a value A, the transmittance rapidly increases because the cavity resonance gain overcomes the photochromic compound absorption loss thus resulting in an increased power of the cavity at the bleaching wavelength. An essentially bleached state occurs in the photochromic material at an incident intensity of B. As the incident intensity is reduced the transmittance follows the curve 21 back to the origin but with an off set transmittance thus forming a hysteris curve.

The device therefore has pairs of stable states, a first on curve 51 equivalent to logic 0 and a second on curve 2 equivalent to logic 1. This is represented in FIG. 1 by the points 31, 41 on curves 51 and 21 which intersect the line X—X. By suitable choice of photochromic material and resonant cavity parameters, switch up and switch down can be induced at different bleaching beam intensities thereby giving rise to one or more bistable states, the number of which is also determined by the photochromic material and cavity parameters and by the maximum intensity of the bleaching radiation.

The present invention may be put into practice in the manner described in our U.K. patent application No. 8519711 (Publication No. 2180360). The arrangement is illustrated in FIG. 2, which is a schematic representation of an optical resonant assembly in accordance with the invention.

Referring to FIG. 2, a Fabry-Perot resonant cavity at an appropriate wavelength is constructed of partially transmitting mirrors 3 and a layer of photochromic material 5 supported on an optically transmitting matrix is placed between the mirrors 3. A beamsplitter 7 is placed before the Fabry-Perot cavity 1 directing a portion of a bleaching beam 9 from a laser to an incident light intensity detector 11 and a portion of the beam 9 to the Fabry-Perot cavity 1 where it is transmitted through the cavity 1 including the photochromic 5 to be collected by a transmitted light intensity detector 13. The outputs from the detecting means 11 and 13 can be compared in order to measure the transmittance level of the photochromic layer at different incident intensities. A series of logic bits can be written to the cavity and a large number of bits can be stored because of the high resolution capacity of the photochromic materials employed. The logic bits can be addressed by deflecting the incident beam 9 or by moving the resonant cavity with respect to the beam.

The resonant devices described herein may be used for any of the uses mentioned in our above U.K. patent specification No. 2180360, except for archival data storage. Nevertheless, the simplicity of operation gained by the requirement for only a single bleaching beam of one or more wavelengths is advantageous in switching operations. Furthermore, the photochromic materials mentioned above enable sharper upwards and downwards transitions to be achieved at the switching points, which implies faster switching speeds.

The bleaching beam may be laser operated in the visible region, e.g. an Argon-ion laser.

We claim:

1. An optical resonant assembly which comprises a plurality of partially light-transmitting mirrors, a layer of photochromic material supported on or in a matrix, which matrix is in the form of a transparent plastic substrate, and disposed between mirrors, a light source providing a single light beam of variable intensity incident on the layer of photochromic material and detecting means for determining transmittance values of said incident beam at different intensity levels, said photochromic material having a low quantum yield for bleaching with light of a wavelength corresponding to the wavelength of said light beam and being selected from pyran compounds of the general formula (I) below:

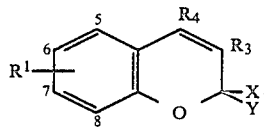
(I)

wherein X and Y together represent a spiro-adamantylidene group or a spiro-carbocyclic or heterocyclic group or X and Y independently represent hydrogen, lower alkyl having 1 to 5 carbon atoms or phenyl and $R_3$ and $R_4$ each independently represent hydrogen, alkyl, aralkyl wherein the alkyl portion is attached to the pyran ring, aryl, halogen or a heterocyclic group and $R^1$ represents hydrogen, lower alkyl having 1 to 5 carbon atoms, aryl, alkoxy, alkyl- or dialkyl amino, halogen, or a heterocyclic group or $R^1$ represents a fused benzene ring at the 5, 6 or 7, 8 positions, said alkyl- or dialkyl amino groups being bound to the pyran ring via their respective nitrogen atoms, whereby said assembly is switchable between a lower and a higher transmission state and vice versa by variation of the intensity of said single light beam with the proviso that said single light beam is the only light beam which illuminates said photochromic layer.

2. A resonant assembly according to claim 1 in which one of X and Y is lower alkyl having 1 to 5 carbon atoms.

3. A resonant assembly according to claim 1 or 2 in which one of X and Y is a phenyl group.

4. A resonant assembly according to claim 1 in which one of X and Y is a phenyl group substituted in the ortho and/or para positions with a primary, secondary or tertiary amino group or with a nitrogen-containing heterocyclic group, wherein the nitrogen is bonded to the phenyl group.

5. A resonant assembly according to claim 1 in which $R_3$ and $R_4$ are both hydrogen.

6. A resonant assembly according to claim 1 in which the photochromic compound is a naphthopyran having one of the following structural formulae:

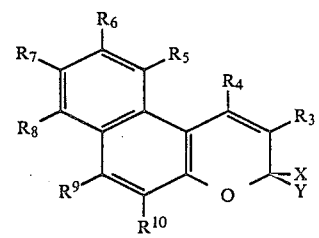

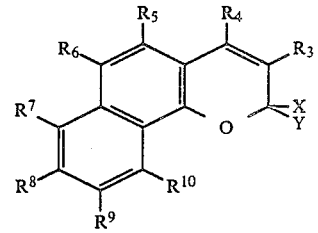

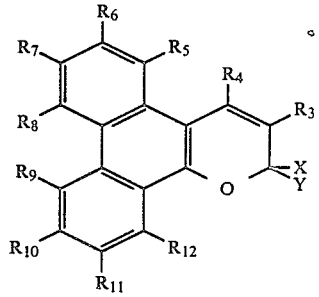

wherein X and Y have the same significance as in claim 1 and $R_1$ to $R_{12}$ each independently represent hydrogen, alkyl, aryl, aralkyl, wherein the alkyl portion is bound to the ring, alkoxy, hydroxy, alkyl- or dialkyl- amino, alkylaminophenyl, halogen or a heterocyclic group, with the proviso that $R_3$ or $R_4$ are not alkoxy, hydroxy, or alkyl- or dialkyl- amino, wherein in the case of alkylaminophenyl, the amino nitrogen is bound to the phenyl group and in the case of the alkyl- or dialkyl- amino groups, these are bound to a ring via their respective amino nitrogen atoms.

7. A resonant cavity according to claim 6 in which a first detecting means is provided for receiving light transmitted by the cavity and second detecting means is provided for receiving light from said source which has not passed through the cavity, whereby a comparison between the relative intensities measured by the first and second detecting means can be used to determine the transmittance value of the photochromic layer at a given intensity.

8. A resonant assembly according to claim 7 wherein the resonant cavity is a Fabry-Perot etalon.

9. A resonant assembly according to claim 8 which has at least two levels of transmittance dependent on the intensity of the incident beam.

10. A resonant assembly according to claim 7 which includes deflecting means for moving the incident light beam relatively to the layer of photochromic material so that different points on the layer can be illuminated.

11. A resonant assembly according to claim 10 wherein said deflecting means comprises means for moving the cavity with respect to the beam.

12. A resonant assembly according to claim 2, in which $R_3$ and $R_4$ are both hydrogen.

13. A resonant assembly according to claim 3, in which $R_3$ and $R_4$ are both hydrogen.

14. A resonant assembly according to claim 4, in which $R_3$ and $R_4$ are both hydrogen.

* * * * *